US00PP29812P3

(12) United States Plant Patent
Moen

(10) Patent No.: US PP29,812 P3
(45) Date of Patent: Nov. 6, 2018

(54) ***GERBERA* PLANT NAMED 'GARSPICE IMP'**

(50) Latin Name: *Gerbera hybrida*
Varietal Denomination: Garspice Imp

(71) Applicant: Melchior Moen, Mijdrecht (NL)

(72) Inventor: Melchior Moen, Mijdrecht (NL)

(73) Assignee: Florist Holland B.V., Aalsmeer (NL)

( * ) Notice: Subject to any disclaimer, the term of this patent is extended or adjusted under 35 U.S.C. 154(b) by 0 days.

(21) Appl. No.: 15/530,622

(22) Filed: Feb. 9, 2017

(65) Prior Publication Data

US 2018/0228068 P1 Aug. 9, 2018

(51) Int. Cl.
*A01H 5/02* (2018.01)

(52) U.S. Cl.
USPC ..... Plt./357

(58) Field of Classification Search
USPC ..... Plt./357
See application file for complete search history.

*Primary Examiner* — Susan Beth McCormick Ewoldt
(74) *Attorney, Agent, or Firm* — C. A. Whealy

(57) ABSTRACT

A new and distinct cultivar of *Gerbera* plant named 'Garspice Imp', characterized by its broadly upright to spreading and uniformly mounding plant habit; dense and bushy appearance; relatively small leaves; numerous inflorescences with red purple and very pale yellow-colored ray florets; upright and moderately strong scapes; and good garden performance.

1 Drawing Sheet

Botanical designation: *Gerbera hybrida.*
Cultivar denomination: 'GARSPICE IMP'.

BACKGROUND OF THE INVENTION

The present invention relates to a new and distinct cultivar of *Gerbera* plant, botanically known as *Gerbera hybrida* and hereinafter referred to by the name 'Garspice Imp'.

The new *Gerbera* plant is a product of a planned breeding program conducted by the Inventor in De Kwakel, The Netherlands. The objective of the breeding program is to create new compact *Gerbera* plants with numerous inflorescences, good garden performance, frost tolerance and attractive inflorescence coloration.

The new *Gerbera* plant is a naturally-occurring whole plant mutation of *Gerbera hybrida* 'Garspice', not patented. The new *Gerbera* plant was discovered and selected by the Inventor as a single flowering plant within a population of plants of 'Garspice' in a controlled greenhouse environment in De Kwakel, The Netherlands in September, 2014.

Asexual reproduction of the new *Gerbera* plant by cuttings and by tissue culture in a controlled environment in De Kwakel, The Netherlands since November, 2014 has shown that the unique features of this new *Gerbera* plant are stable and reproduced true to type in successive generations.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Garspice Imp'. These characteristics in combination distinguish 'Garspice Imp' as a new and distinct *Gerbera* plant:

1. Broadly upright to spreading and uniformly mounding plant habit.
2. Dense and bushy appearance.
3. Relatively small leaves.
4. Numerous inflorescences with red purple and very pale yellow-colored ray florets.
5. Upright and moderately strong scapes.
6. Good garden performance.

Plants of the new *Gerbera* differ from plants of the parent, 'Garspice', in the following characteristics:

1. Plants of the new *Gerbera* are more vigorous than plants of 'Garspice'.
2. Plants of the new *Gerbera* have larger leaves than plants of 'Garspice'.
3. Plants of the new *Gerbera* have larger inflorescences than plants of 'Garspice'.

Plants of the new *Gerbera* can be compared to plants of the *Gerbera hybrida* 'Gardreams', disclosed in U.S. Plant Pat. No. 26,636. Plants of the new *Gerbera* differ from plants of 'Gardreams' in the following characteristics:

1. Ray florets of plants of the new *Gerbera* are shorter and narrower than ray florets of 'Gardreams'.
2. Plants of the new *Gerbera* and 'Gardreams' differ in ray floret color as plants of 'Gardreams' have solid red purple-colored ray florets.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant. The photograph comprises a side perspective view of a typical flowering plant of 'Garspice Imp' grown in a container.

DETAILED BOTANICAL DESCRIPTION

The aforementioned photograph and following observations and measurements describe plants grown during the autumn and winter in 13-cm containers in a glass-covered greenhouse in De Kwakel, The Netherlands and under cultural practices typical of commercial *Gerbera* production. During the production of the plants, day temperatures ranged from 10° C. to 16° C. and night temperatures ranged from 10° C. to 12° C. Rooted tissue-cultured plants were 16 and 26 weeks old when the description and photograph, respectively, were taken. In the following description, color references are made to The Royal Horticultural Society Colour Chart, 2015 edition, except where general terms of ordinary dictionary significance are used.

Botanical classification: *Gerbera hybrida* 'Garspice Imp'.

Parentage: Naturally-occurring whole plant mutation of *Gerbera hybrida* 'Garspice', not patented.

Propagation:

*Type*.—By meristem culture.

*Time to initiate roots, summer and winter*.—About 2.5 to 3 weeks at temperatures about 20° C.

*Time to produce a rooted young plant, summer and winter*.—About 5 to 6 weeks at temperatures about 20° C. to 26° C.

*Root description*.—Fibrous; white in color.

Plant description:

*Appearance*.—Herbaceous perennials that are typically grown as container or garden plants; uniformly mounding plant habit, broadly upright to spreading and roughly flattened globular in shape; numerous leaves arranged in basal rosettes and outwardly arching; dense and bushy habit; inflorescences held above the foliar plane on upright and moderately strong basal scapes; moderately vigorous growth habit and moderate growth rate.

*Plant height, soil level to top of foliar plane*.—About 23 cm.

*Plant height, soil level to top of inflorescences*.—About 41.5 cm.

*Plant width*.—About 42.8 cm.

Leaf description:

*Arrangement*.—Alternate, simple.

*Length*.—About 16.6 cm.

*Width*.—About 16.6 cm.

*Shape*.—Narrowly ovate; runcinate.

*Apex*.—Broadly acute.

*Base*.—Acuminate.

*Margin*.—Coarsely and irregularly angulate; sinuses medium to deep and divergent; undulate.

*Texture, upper surface*.—Moderately pubescent; slightly rugose.

*Texture, lower surface*.—Moderately to densely pubescent; slightly rugose.

*Luster, upper surface*.—Moderately glossy.

*Luster, lower surface*.—Matte.

*Venation pattern*.—Pinnate.

*Color*.—Developing leaves, upper surface: Close to between 141A and 143A. Developing leaves, lower surface: Close to 191C. Fully expanded leaves, upper surface: Close to between NN137A and 147A; venation, close to 147B. Fully expanded leaves, lower surface: Close to 144A; venation, close to 145A to 145B.

*Petioles*.—Length: About 9.7 cm. Diameter: About 4 mm. Strength: Moderate to high. Texture: Moderately pubescent. Luster: Slightly glossy. Color, upper and lower surfaces: Close to 144A.

Inflorescence description:

*Appearance*.—Composite inflorescence form with oblanceolate-shaped ray florets; solitary inflorescences borne on upright and strong scapes above the foliar plane; ray and disc florets arranged acropetally on a capitulum.

*Fragrance*.—None detected.

*Flowering season*.—Plants begin flowering about three months after planting; under garden conditions in The Netherlands, plants flower from early spring to late summer; plants can be flowered year-round in the greenhouse.

*Inflorescence longevity*.—Depending on the temperature, inflorescences last about three weeks on the plant; inflorescences persistent.

*Quantity of inflorescences*.—Moderate to freely flowering habit with about seven open and developing inflorescences per plant at one time.

*Inflorescence buds*.—Height: About 1.8 cm. Diameter: About 2 cm. Shape: Roughly globular. Texture: Moderately pubescent. Luster: Very slightly glossy Color: Close to 138A and 138B; immature ray florets, close to between 145C and 150C.

*Inflorescence size*.—Diameter: About 7.9 cm. Depth (height): About 2.8 cm. Diameter of disc: About 2.8 cm. Receptacle height: About 3 mm. Receptacle diameter: About 5 mm. Receptacle color: Close to 157D.

*Ray florets*.—Quantity and arrangement: About 70 per inflorescence arranged in about three whorls. Orientation: About 40° from horizontal. Length: About 3.8 cm. Width: About 7 mm. Shape: Oblanceolate. Apex: Finely emarginate to finely praemorse. Base: Narrowly cuneate. Margin: Entire. Texture, upper surface: Smooth, glabrous; velvety. Texture, lower surface: Smooth, glabrous; slightly velvety. Luster, upper surface: Matte. Luster, lower surface: Very slightly glossy. Color: When opening, upper surface: Close to 67B; towards the base, close to 67D; at the base, close to 2D. When opening, lower surface: Close to 1C blotched with close to 60C to 60D. Fully opened, upper surface: Close to N66A; towards the base, close to between 2D and 4D; colors do not fade with development. Fully opened, lower surface: Close to 59D; longitudinal stripes, close to 62C and 62D; colors do not fade with development.

*Disc florets*.—Quantity and arrangement: About 320 spirally arranged at center of receptacle in about 13 whorls. Length: About 1.2 cm. Width: About 3.5 mm. Shape: Tubular with two free distal lobes. Apex: Acute. Base: Lower 60%, fused. Margin: Entire. Texture, inner and outer surfaces: Smooth, glabrous; slightly velvety. Luster, inner surface: Matte. Luster, outer surface: Very slightly glossy. Color: When opening, inner and outer surfaces: Close to 8D. Fully opened, inner surface: Close to 8D; apex, tinged with close to 35D; colors do not fade with development. Fully opened, outer surface: Close to 8D; color does not fade with development.

*Pappus*.—Quantity of hairs per floret: About 60. Length: About 7 mm. Diameter: Less than 1 mm. Texture: Soft. Color: Close to 162C to 162D; apex, close to 185D.

*Phyllaries*.—Quantity and arrangement: About 60 per inflorescence arranged in about three whorls.

Length: About 1.2 cm. Width (at base): About 2.5 mm. Shape: Lanceolate. Apex: Narrowly acute. Base: Cuneate. Margin: Entire. Texture, upper surface: Smooth, glabrous. Texture, lower surface: Moderately pubescent. Luster, upper surface: Moderately glossy. Luster, lower surface: Slightly glossy. Color, upper surface: Close to 144A. Color, lower surface: Close to 143A.

*Scapes*.—Length: About 37.4 cm. Diameter: About 6 mm; distally, about 4 mm. Angle: Mostly upright, about 8° from vertical. Strength: Moderately strong. Texture: Densely pubescent. Luster: Moderately glossy. Color: Close to 144A; distally, close to 147B.

*Reproductive organs*.—Androecium (present on disc florets only): Quantity per floret: Five. Filament length: About 8 mm. Filament color: Close to 8D. Anther shape: Lanceolate. Anther length: About 3 mm. Anther width: About 0.3 mm. Anther color: Close to 14A to 14B. Pollen amount: Scarce. Pollen color: Close to 11A. Gynoecium (present on ray and disc florets): Quantity per floret: One. Pistil length: About 1.1 cm. Stigma shape: Cleft. Stigma color: Close to 155A. Style length: About 1 cm. Style color: Close to 155D. Ovary color: Close to NN155A.

*Seeds and fruits*.—To date, seed and fruit production has not been observed on plants of the new *Gerbera*.

Disease & pest resistance: Resistance to pathogens and pests common to *Gerbera* plants has not been observed on plants of the new *Gerbera* grown under commercial production conditions.

Garden performance: Plants of the new *Gerbera* have been observed to have good garden performance, to tolerate high temperatures about 35° C. and to be cold hardy to USDA Hardiness Zone 7.

It is claimed:

1. A new and distinct *Gerbera* plant named 'Garspice Imp' as illustrated and described.

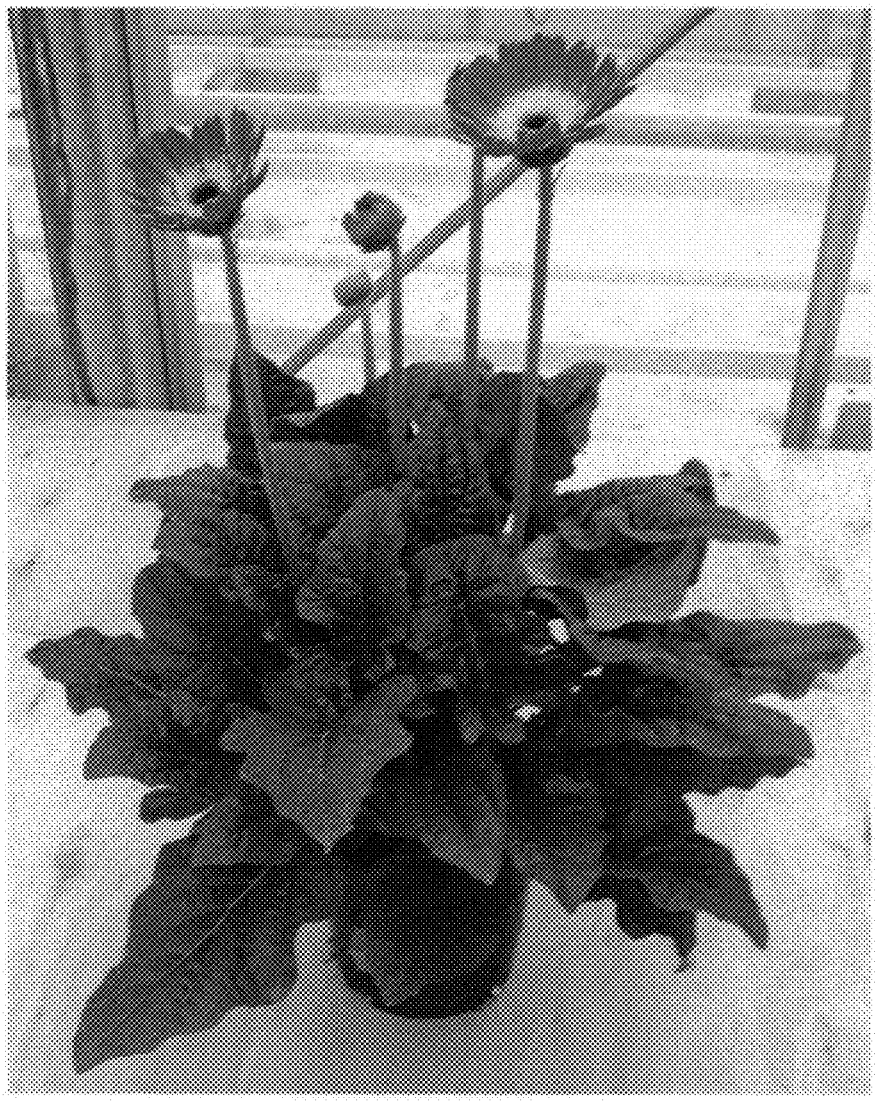

* * * * *